United States Patent [19]  [11] 3,995,019
Jerome [45] Nov. 30, 1976

[54] DIAGNOSTIC REAGENT SYSTEM

[75] Inventor: Frederick R. Jerome, Anaheim, Calif.

[73] Assignee: Baxter Travenol Laboratories, Inc., Deerfield, Ill.

[22] Filed: Mar. 4, 1975

[21] Appl. No.: 555,215

[52] U.S. Cl. .............................. 424/1.5; 23/230 B; 252/301.1 R; 424/12; 424/85; 424/88
[51] Int. Cl.² .................. A61K 43/00; G01N 33/00; G01T 1/16
[58] Field of Search ............. 424/1, 12, 85, 88, 359; 23/230 B; 252/301.1 R

[56] References Cited
UNITED STATES PATENTS 3,415,804 12/1968 Polson .............................. 424/85 X
3,862,302 1/1975 Price et al ............................ 424/12

Primary Examiner—Benjamin R. Padgett
Assistant Examiner—Christine M. Nucker
Attorney, Agent, or Firm—Paul C. Flattery; Lawrence W. Flynn; Max D. Hensley

[57] ABSTRACT

A solid phase reagent for use in radioimmunoassay of antigens and antibodies prepared by admixing specific antibody or radiolabeled antigen with polyethylene glycol and gamma globulin in buffer at pH 4–10 and lyophilizing.

32 Claims, 2 Drawing Figures

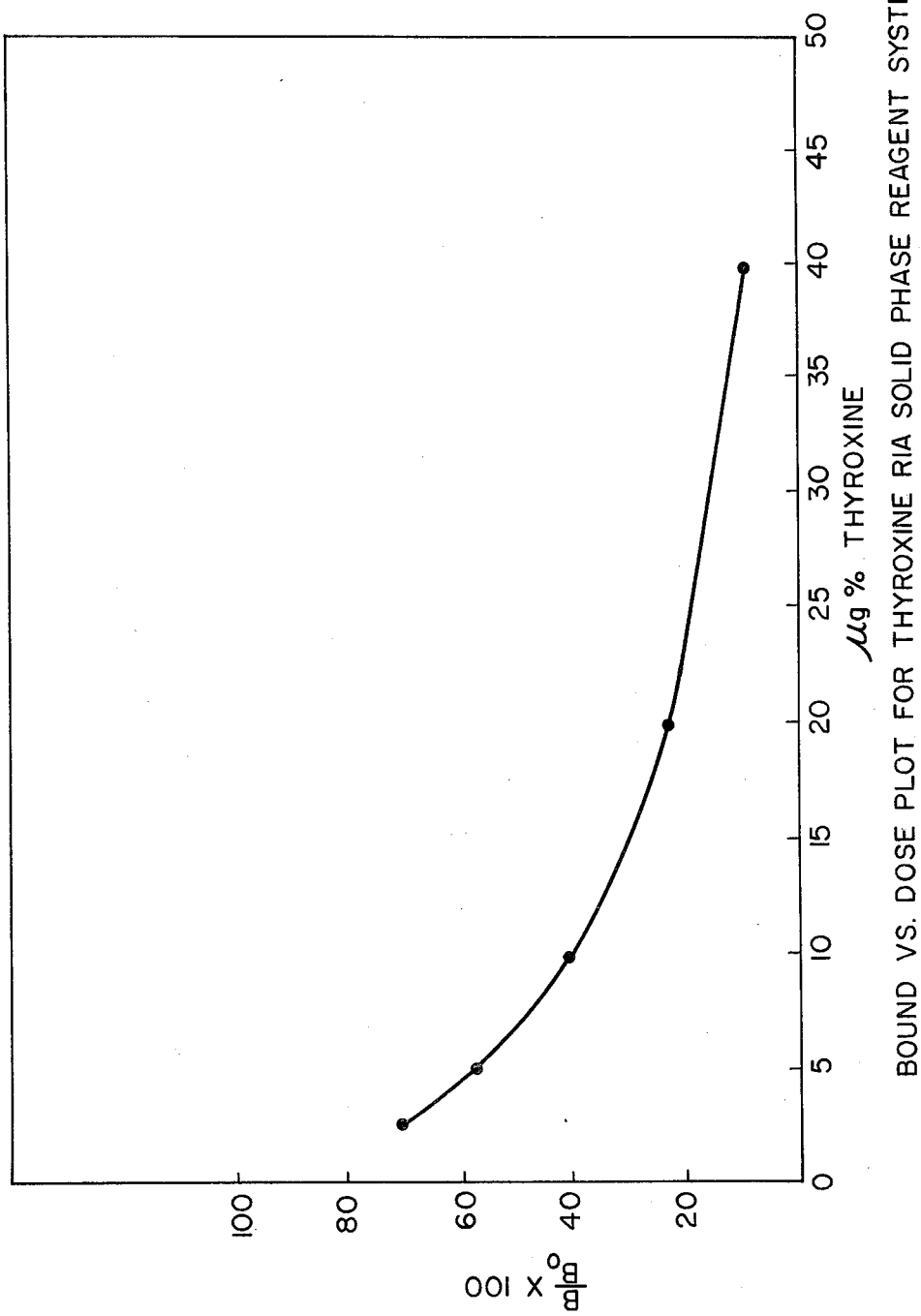

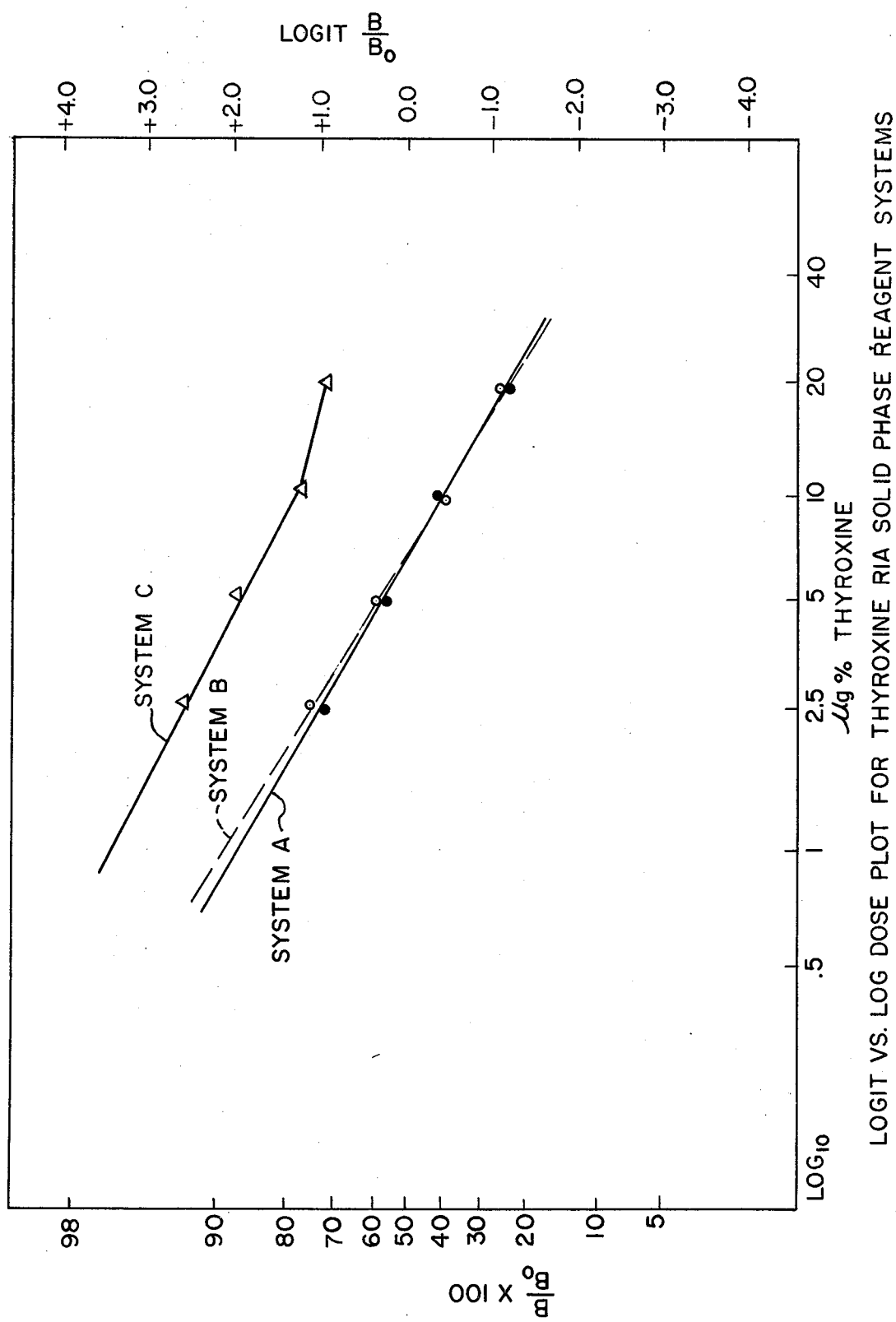

DIAGNOSTIC REAGENT SYSTEM

This invention relates to a reagent and method for use in the determination of antigens, antibodies, enzymes and other proteins and polypeptides, hormones and similar such substances having biological activity.

In recent years a number of clinical diagnostic tests have been developed which employ radioisotope labeled materials. These tests have been adapted to the determination of small concentrations of various components of blood serum and other biological fluids. In the diagnostic technique known as radioimmunoassay (RIA), antigen is measured by its effect on the binding of a small quantity of radioactive tracer antigen to a predetermined amount of specific antibody. This RIA technique must include some procedure for separating antibody-bound tracer from the unbound tracer after completion of the immune reaction, whereby the radioactivity of the separated components can be determined by scintillation counting.

Various procedures have been developed heretofor for separating the bound and unbound tracer components in RIA techniques. According to one conventional procedure, selective adsorption of the free tracer component is achieved by the use of a particulate adsorbent such as charcoal as disclosed in U.S. Pat. No. 3,442,819, or by the use of inorganic crystalline adsorbents in colloidal form such as magnesium carbonate or silicas as described in U.S. Pat. Nos. 3,666,854, 3,721,528 and 3,776,698. Another known procedure employs ion exchange resins having strongly basic amino or quaternary ammonium groups as disclosed in U.S. Pat. No. 3,414,383, or employs the resin in a polyurethane sponge such as described in U.S. Pat. No. 3,206,602. Still other methods employ covalent bonding of the antibody to water insoluble polymers such as dextran and Sephadex (a trademark of Pharmacia AB, Uppsala, Sweden) as set forth in U.S. Pat. No. 3,555,143; or a nonspecific physical bonding to various polymers as mentioned in U.S. Pat. No. 3,790,663; or entrapment in a gel material such as acrylamide as seen from U.S. Pat. No. 3,793,445.

Recently, a procedure has been reported which employs polyethylene glycol as a precipitating agent for separating the bound and unbound components in RIA techniques; Desbuquois and Aurbach, *J. Clin. Endocrinol. Metab.* 33, 732 (1972); Barrett and Cohen, *Clin. Chem.* 18, 1339 (1972); and Creighton et al., *J. Immunol.* 111, 1219 (1973). In this procedure, the polyethylene glycol is added to the test materials after the step of binding by incubation over a period of time. The polyethylene glycol then precipitates the radiolabeled antibody-bound component from the unbound component. While this procedure is useful, it involves numerous steps and inconvenient handling of several components by the laboratory technologist. High nonspecific counts (radiolabeled antigen not bound to antibody) are associated with this technique.

In accordance with the present invention, as distinguished from the prior art, polyethylene glycol is employed in a solid phase reagent and method for radioimmunoassay whereby only this single reagent is required and no precipitation reaction, which is initimatly involved with the specific antibody, need be carried out by the laboratory technologist after reconstitution of the solid phase reagent. The invention utilizes a combination of a specific antibody and/or a radiolabeled antigen and the polyethylene glycol together with a gamma globulin carrier buffered to a suitable pH in a lyophilized solid phase system. This lyophilized product can be supplied to the clinical laboratory for use in a convenient and rapid RIA test which requires only reconstitution and addition of the patient's serum being tested.

A principal advantage of the present invention is a reduction in the number of steps necessary for RIA by the laboratory technologist, including elimination of the addition of a separating agent and subsequent treatment thereof at the end of the immune reaction. Another significant advantage of this invention is that denaturation of the antibody is minimized because there is no bonding of active sites on the antibody such as occurs with covalent, ionic or non-specific bonding of polymers. The reliability of the RIA is thus increased by a reduction in the number of errors which are likely to occur in numerous pipetting steps or by denaturation of the antibody as occurs according to prior procedures.

It has also been found that the solid phase system of this invention more nearly simulates a homogeneous solution phase than other solid phase systems. This system thereby desirably provides a large surface area without loss of its heterogeneity for reaction with minimal loss of antibody activity.

The lyophilized solid phase single reagent also is particularly well adapted to convenient shipping insofar as it involves a less readily disturbed material and fewer reagents than heretofor.

In the accompanying drawing:

FIG. 1 is a standard curve showing the radioactive counts per minute of bound antigen (thyroxine) plotted as a function of thyroxine concentration (in standard units of microgram percent) in a representative example of the RIA solid phase reagent system defined herein.

FIG. 2 shows the three representative RIA reagent systems A, B and C of Example 1 In which standard curves (of the type of FIG. 1) have been linearized by logit transformation.

In general, three RIA lyophilized solid phase systems are provided in accordance with the present invention. In one embodiment, specific antibody is provided in combination with the polyethylene glycol and gamma globulin carrier. In a second embodiment, radiolabeled antigen is provided in combination with the polyethylene glycol and gamma globulin carrier. In a third embodiment, both specific antibody and radiolabeled antigen are provided in combination with the polyethylene glycol and gamma globulin carrier.

In the preferred embodiments of the invention, the radiolabeled antigen is provided in the reconstituting fluid. These embodiments have the additional advantage over the prior art in that precision of the RIA test is increased by virtue of the larger volume from which the radiolabeled antigen is dispensed. According to prior procedures which do not provide for reconstitution of a solid phase reagent, the radiolabeled antigen must be added in a very small quantity and, thus, the liklihood of error is greater than according to the present procedure.

In the preferred embodiments of the invention, about three parts by volume of a 0.01%–5% solution of gamma globulin carrier and about five parts by volume of a 5%–50% solution of polyethylene glycol are provided in combination with about one part by volume of a solution of either the specific antibody which has been titered to bind from about 10%–90% of the appropriate radiolabeled antigen in an amount of about $10_{pg}$–$10_{ng}$ or about one part by volume of a solution of the radiolabeled antigen in an amount of about $10_{pg}10_{ng}$ or a combination with about one part by volume of a solution each of the radiolabeled antigen and the specific antibody.

pg = picogram
ng = nanogram

The polyethylene glycol polymer used in this invention generally has a molecular weight of from about 200 to about 10,000 and preferably from about 4000 to about 6000. It can be conveniently incorporated in the solid-phase system of this invention by prior admixture to form an aqueous solution containing from about 5% to about 50% (wt./vol.) polyethylene glycol and preferably about 30% of this polymer.

Various known sources of gamma globulin can be used for obtaining the gamma globulin carrier used in this invention and a preferred source is Cohn II Human Plasma Fraction which is rich in IgG. Other suitable sources are ammonium sulfate fractionated serum and bovine gamma globulin fraction. For incorporation into the solid phase system of this invention, the gamma globulin preferably is diluted in an aqueous buffer solution having a pH of from about 4 to about 10 at a concentration of from about 0.01% to about 5% (wt./vol.) and preferably about 3.2%.

The specific antibody to antigen to be assayed is diluted to permit ideal stoichiometric association with the antigen being assayed as to give optimum assay sensitivity. Examples of such antigens which can be assayed in accordance with the present invention are thyroxine, triiodothyronine, digoxin and digitoxin. This dilution preferably is made with buffer material similar to that used for diluting the gamma globulin carrier set forth above.

The above examples of antigens are not limiting but are set forth only for illustrative purposes. Small molecules such as steroids, drugs and peptides can be readily adapted for use in this invention as well as small and large proteins, viruses, nucleic, acids, for example, angiotension I and II, aldosterone, thyroid stimulating hormone (TSH) and thyroxine binding globulin (TBG), and other compounds such as will be apparent to the person skilled in the art.

Radiolabeled antigens which can be used for the aforesaid specific antibodies are, for example, $125_{I\text{-}thyroxine}$, $125_{I\text{-}triiodothyronine}$, $125_{I\text{-}digoxin}$ and $125_{I\text{-}digitoxin}$. All of these radiolabled antigens are available commercially. Other radioisotopes which can be used to prepare radiolabeled antigens suitable for use in this invention are, for example, $^{131}I$, $^{3}H$, $^{14}C$, and $^{57}Co$. The antigen preferably is labeled with $^{125}I$ or other radioisotope to a specific activity of from about one to about 1000 microcuries per microgram ($\mu$ curies/$\mu$g) of antigen. The radiolabeled antigen also preferably is diluted in buffer material similar to that used for diluting the gamma globulin carrier set forth above. This dilution depends upon the initial specific activity and the desired disintegrations per minute (dpm) required to realize optimum counting and sensitivity of the assay.

Examples of buffers which can be employed for the foregoing dilution are barbital, tris, phosphate, and borate buffers having the aforesaid pH of about 4 to about 10. A preferred buffer is a barbital buffer comprising 0.08 molar sodium barbital and 0.1% (wt./vol.) bovine serum albumin, pH 8.4.

When using the thyroxine or triiodothyronine antigens, the buffer also preferably contains ammonium or sodium 8-anilinonaphthalene-1-sulfonate or the free acid (ANS) as an uncoupler of the antigen from thyroxine-binding globulin (TBG). This uncoupler material is used in the buffer at a concentration of 0.1% to about 0.95% and preferably 0.35% (wt./vol.). The thyroxine and triiodothyronine antigens also preferably are labeled with radioisotope to a specific activity of from about 50 to about 100 $\mu$ curies/$\mu$g of antigen.

Lyophilization of any of the foregoing three RIA reagent systems can be carried out by any conventional lyophilization techniques and is preferably carried out in conventional plastic or glass test tubes which can then be directly used in the RIA test procedures by the laboratory technologist.

The RIA test procedure will vary, depending upon which of the aforesaid three lyophilized solid phase systems is employed. Thus, when the RIA solid phase system contains specific antibody, the reconstituting solution should contain the radiolabeled antigen, whereas when the RIA solid phase system contains radiolabeled antigen, the reconstituting solution should contain the specific antibody. When the RIA solid phase system contains both specific antibody and radiolabeled antigen, the reconstituting solution can be distilled water. About 1000 microliters ($\mu$l) of reconstituting solution can be used for about 0.15 grams of the lyophilized RIA solid phase system per tube. Any conventional tube size may be used, however, 12 mm by 75 mm is preferred.

Following reconstitution, the patient's serum or other unknown is added to the reconstituted RIA solid phase system, preferably in an amount of from about 25 to about 200$\mu$ l. The amount of serum depends generally on the test being employed. For thyroxine, 25$\mu$ l of serum preferably is utilized. When greater than about 200$\mu$ l of patient's serum is used in the test procedure, it is generally unnecessary to employ gamma globulin in the solid phase reagent as sufficient gamma globulin is already present in the patient's sample. The mixture of the reconstituted RIA solid phase system and patient's serum is then incubated for about 30 to about 60 minutes at about 37° C, cooled to room temperature and centrifuged. The supernatant is decanted or aspirated and the radioactivity in the remaining precipitate is counted with a scintillation counter or gamma spectrometer.

Control standards are run in parallel with the unknown samples and a standard curve is prepared therefrom. These control standards contain predetermined concentrations of the antigen or antibody being assayed. For example, a graded series of five control standards in an amount of 25$\mu$ l each and containing, respectively, 0, 2.5, 5, 10 and 20 microgram percent ($\mu$g %) of thyroxine can be used to prepare a standard curve for thyroxine. The concentration of thyroxine in the unknown is then determined by plotting the values obtained for the unknown on the standard curve.

The calculations which are performed are based on conventional methodology. The counts in the tube which contain antigen free serum (control standard with zero antigen) are set to 100% (defined as $B_o$). As antigen in the standard is increased, the counts (defined as B) decrease in the precipitate and these counts are divided by the counts in the zero tube to give $B/B_o$ values. The $B/B_o$ values can be plotted against mg. % of antigen on linear graph paper. A typical standard curve is depicted in FIG. 1. In FIG. 2, the logit transformation of $B/B_o$ and log of antigen concentration is used to convert the sigmoid curve into a straight line.

In some instances it may be desirable to provide a non-specific control standard which does not contain any specific antibody in either the RIA solid phase reagent or in the reconstituting solution. This control standard may be used to ascertain the radiolabeled antigen non-specifically trapped or occluded to the solid phase reagent. In these instances, the true bound tracer is determined by subtracting the nonspecific counts from all samples.

The following examples will further illustrate the invention although it will be appreciated that the invention is not limited to these specific examples.

EXAMPLE 1

A solid phase reagent for use in radioimmunoassay of thyroxine antibody is prepared from the following aqueous reagents:
 a. Barbital buffer — 0.08 molar sodium barbital, pH 8.4.
 b. Barbital-BSA — 0.08 molar sodium barbital, 0.1% (wt./vol.) bovine serum albumin (BSA), pH 8.4.
 c. ANS — 0.35% (wt./vol.) 8-anilino-1-naphthalene sulfonic acid (ANS) in the above barbital-BSA solution.
 d. IgG — 3.2% (wt./vol.) Cohn II Human Plasma Fraction, in the above barbital-BSA solution.
 e. Specific Antibody — Antibody to thyroxine, diluted with the above barbital-BSA solution to bind approximately 40% of radiolabeled thyroxine.
 f. Radiolabeled Antigen — $^{125}$I-thyroxine, diluted with the above barbital-BSA solution to about 150 pg (approx. 40,000 cpm) per ml.
 g. Polyethylene Glycol — 30% polyethylene glycol (wt./vol.) having mol. wt. about 6000, in distilled water.

A solution of gamma globulin carrier is then prepared by admixing one part by volume of each of the three foregoing solutions of (b) Barbital-BSA, (c) ANS, and (d) IgG.

Combined solutions are then prepared from the foregoing reagents for three RIA test systems as follows:

| | Reagent | Proportions By Volume |
| --- | --- | --- |
| Reagent System (A) | Gamma Globulin Carrier | 3 |
| | Specific Antibody | 1 |
| | Polyethylene Glycol | 5 |
| Reagent System (B) | Gamma Globulin Carrier | 3 |
| | Radiolabeled Antigen | 1 |
| | Polyethylene Glycol | 5 |
| Reagent System (C) | Gamma Globulin Carrier | 3 |
| | Specific Antibody | 1 |
| | Radiolabeled Antigen | 1 |
| | Polyethylene Glycol | 5 |

The above prepared RIA reagent systems are then dispensed into plastic 12 mm by 75 mm test tubes using 900μl per tube of either RIA Reagent System (A) or RIA Reagent System (B) or 1000μl per tube of RIA Reagent System (C). The solutions are then lyophilized to a solid, dry pack in the tubes.

The foregoing solid phase are used in radioimmunoassay tests as follows

Reagent System (A)

1. Add 1000 μl of reagent (f), radiolabeled antigen, to each tube containing lyophilized Reagent System (A).
2. Add 25μl of control standard or patient's blood serum.
3. Incubate 30 minutes at 37° C.
4. Cool to room temperature (ca. 25° C) and centrifuge at 3000 rpm for ten minutes.
5. Decant the liquid phase.
6. Count radioactivity in the precipitate with a gamma spectrometer.

The standard curve obtained is illustrated in FIG. 2.

Reagent System (B)

1. Add 1000 μl of reagent (e), specific antibody, to each tube containing lyophilized Reagent System (B).
2. Add 25μl of control standard patient's blood serum.
3. Incubate 30 minutes at 37° C.
4. Cool to room temperatue (ca. 25° C) and centrifuge at 3000 rpm for ten minutes.
5. Decant the liquid phase.
6. Count radioactivity in the precipitate with a gamma spectrometer.

The standard curve obtained is illustrated in FIG. 2.

Reagent System (C)

1. Add 1000μl of distilled water to each tube containing lyophilized Reagent System (C).
2. Add 25 μl of control standard or patient's blood serum.
3. Incubate 30 minutes at 37° C.
4. Cool to room temperature (ca. 25° C) and centrifuge at 3000 rpm for ten minutes.
5. Decant the liquid phase.
6. Count radioactivity in the precipitate with a gamma spectrometer.

The standard curve obtained is illustrated in FIG. 2.

For each of the foregoing tests, control standards (as illustrated above) are run in which solutions of predetermined concentrations of thyroxine are substituted for the patient's serum. The concentration of thyroxine in the patient's sample is then determined by comparison with the standard curve prepared from the values plotted for the control standards.

EXAMPLE 2

Example 1 is repeated except that antibody to triiodothyronine and $^{125}$I-triiodothyronine are substituted for antibody to thyroxine and $^{125}$I-thyroxine, respectively, and the amount of serum used for this test is 200μl.

EXAMPLE 3

Example 1 is repeated except that antibody to digoxin and $^{125}$I-digoxin are substituted for antibody to thyroxine and $^{125}$I-thyroxine, respectively.

EXAMPLE 4

Example 1 is repeated except that antibody to digitoxin and $^{125}$I-digitoxin are substituted for antibody to thyroxine and $^{125}$I-thyroxine, respectively.

Various other examples and modifications of the foregoing examples can be devised by the person skilled in the art after reading the foregoing disclosure without departing from the spirit and scope of the invention and it is intended that all such further examples and modifications be included in the appended claims.

What is claimed is:

1. A solid phase reagent for use in radioimmunoassay of antigens and antibodies comprising a lyophilized admixture of (a) material selected from the group consisting of specific antibody radiolabeled antigen, and the combination of specific antibody and radiolabled antigen, (b) polyethylene glycol having a molecular weight of from about 200 to about 10,000 and (c) gamma globulin, said admixture containing buffer having a pH of from about 4 to about 10.

2. The reagent of claim 10 in which the polyethylene glycol has a molecular weight of from about 4000 to about 6000.

3. The reagent of claim 1 in which three parts of (c) and five parts of (b) are admixed with one part of specific antibody or radiolabeled antigen or one part each of specific antibody and radiolabeled antigen.

4. The reagent of claim 1 in which the antigen is selected from the group consisting of thyroxine, triiodothyronine, digoxin and digitoxin.

5. The reagent of claim 1 in which the antibody is specific to an antigen selected from the group consisting of thyroxine, triiodothyronine digoxin and digitoxin.

6. The reagent of claim 1 in which the radiolabel is $^{125}I$ with a specific activity of about one of 1000 $\mu$ curies per $\mu$ gram of antigen.

7. The reagent of claim 1 in which the buffer is a barbital buffer, pH 8.4.

8. The reagent of claim 7 in which the buffer comprises about 0.08 molar sodium barbital and about 0.1% bovine serum albumin.

9. The reagent of claim 8 in which the buffer additionally contains about 0.35% 8-anilino-1-napthalene sulfonic acid or the sodium or ammonium salt thereof.

10. A solid phase reagent for use in radioimmunoassay of antigens and antibodies comprising a lyophilized admixture of (a) material selected from the group consisting of radiolabeled antigen and the combination of specific antibody and radiolabeled antigen, (b) polyethylene glycol having a molecular weight of from about 200 to about 10,000 and (c) gamma globulin, said admixture containing buffer having a pH of from about 4 to about 10.

11. The reagent of claim 10 wherein the material is radiolabeled antigen.

12. A solid phase reagent for use in radioimmunoassay of antigens comprising a lyophilized admixture of (a) specific antibody, (b) polyethylene glycol having a molecular weight of from about 200 to about 10,000, (c) gamma globulin and (d) a buffer having a pH of from about 4 to about 10.

13. A method for the preparation of a solid phase reagent for use in radioimmunoassay of antigens and antibodies comprising admixing (a) material selected from the group consisting of specific antibody, radiolabeled antigen, and the combination of specific antibody and radiolabeled antigen, (b) polyethylene glycol having a molecular weight of from about 200 to about 10,000 and (c) gamma globulin, in aqueous solution containing buffer having a pH of from about 4 to about 10, followed by lyophilizing the mixture.

14. The method of claim 1 in which the polyethylene glycol has a molecular weight of from about 4000 to about 6000.

15. The method of claim 1 in which three parts of (c) and five parts of (b) are admixed with one part of specific antibody or radiolabeled antigen or one part each of specific antibody and radiolabeled antigen.

16. The method of claim 1 in which the antigen is selected from the group consisting of thyroxine, triiodothyronine, digoxin and digitoxin.

17. The method of claim 13 in which the antibody is specific to an antigen selected from the group consisting of thyroxine, triiodothyronine, digoxin and digitoxin.

18. The method of claim 1 in which the radiolabel is 125I with a specific activity of about one to 1000 $\mu$ curies per $\mu$ gram of antigen.

19. The method of claim 1 in which the buffer is a barbital buffer, pH 8.4.

20. The method of claim 19 in which the buffer comprises about 0.08 molar sodium barbital and about 0.1% bovine serum albumin.

21. The method of claim 20 in which the buffer additionally contains about 0.35% 8-anilino-1-napthalene sulfonic acid or the sodium or ammonium salt thereof.

22. A method for the preparation of a solid phase reagent for use in radioimmunoassay of antigen comprising admixing (a) specific antibody, (b) polyethylene glycol having a molecular weight of from about 200 to about 10,000 and (c) gamma globulin, in aqueous solution containing buffer having a pH of from about 4 to about 10, followed by lyophilizing the mixture.

23. A method of radioimmunoassay of antigens and antibodies by solid phase polymeric reaction, comprising combining the solid phase reagent of Claim 10 with aqueous diluent and the patient's serum, incubating to produce liquid and solid phases, separating the phases, and counting the radioactivity.

24. The method of claim 23 in which the polyethylene glycol has a molecular weight of from about 4000 to about 6000.

25. The method of claim 23 in which three parts of (c) and five parts of (b) are admixed with one part of specific antibody or radiolabeled antigen or one part each of specific antibody and radiolabeled antigen.

26. The method of claim 23 in which the antigen is selected from the group consisting of thyroxine, triiodothyronine, digoxin and digitoxin.

27. The method of claim 23 in which the antibody is specific to an antigen selected from the group consisting of thyroxine, triiodothyronine, digoxin and digitoxin.

28. The method of claim 23 in which the radiolabel is $^{125}I$ with a specific activity of about one to 1000 $\mu$ curies per $\mu$ gram of antigen.

29. The method of claim 23 in which the buffer is a barbital buffer, pH 8.4.

30. The method of claim 29 in which the buffer comprises about 0.08 molar sodium barbital and about 0.1% bovine serum albumin.

31. The method of claim 30 in which the buffer additionally contains about 0.35% 8-anilino-1-napthalene sulfonic acid or the sodium or ammonium salt thereof.

32. In the method of radioimmunoassay of antigen wherein (1) a sample suspected to contain antigen, (2) radiolabeled antigen and (3) specific antibody are combined and incubated, thus producing liquid and solid phases, the phases separated and the radioactivity counted, the improvement comprising providing said specific antibody in solid phase admixture with (a) polyethylene glycol having a molecular weight of from about 200 to about 10,000, (b) gamma globulin and (c) a buffer having a pH of from about 4 to about 10.

* * * * *